(12) United States Patent
Verhoeven et al.

(10) Patent No.: US 7,442,205 B2
(45) Date of Patent: Oct. 28, 2008

(54) STENTS AND METHODS FOR PREPARING STENTS FROM WIRES HAVING HYDROGEL COATING LAYERS THEREON

(75) Inventors: Michel Verhoeven, Maastricht (NL); Linda Lee Cahalan, Nashua, NH (US); Patrick Cahalan, Nashua, NH (US); Vincent Larik, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 11/181,495

(22) Filed: Jul. 13, 2005

(65) Prior Publication Data

US 2005/0251250 A1    Nov. 10, 2005

Related U.S. Application Data

(62) Division of application No. 09/721,881, filed on Nov. 27, 2000, now abandoned.

(51) Int. Cl.
*A61F 2/06*    (2006.01)
(52) U.S. Cl. .................... 623/1.46; 623/1.42; 424/423
(58) Field of Classification Search ....... 623/1.11–1.48; 424/423
See application file for complete search history.

(56) References Cited

U.S. PATENT DOCUMENTS

| | | |
|---|---|---|
| 4,795,458 A | 1/1989 | Regan |
| 4,886,062 A | 12/1989 | Wiktor |
| 5,059,166 A | 10/1991 | Fischell et al. |
| 5,163,958 A | 11/1992 | Pinchuk |
| 5,330,500 A | 7/1994 | Song |
| 5,336,518 A | 8/1994 | Narayanan et al. |
| 5,356,433 A | 10/1994 | Rowland et al. |
| 5,449,372 A | 9/1995 | Schmaltz et al. |
| 5,464,650 A | 11/1995 | Berg et al. |
| 5,525,356 A | 6/1996 | Jevne et al. |
| 5,527,354 A | 6/1996 | Fontaine et al. |
| 5,545,211 A | 8/1996 | An et al. |
| 5,554,181 A | 9/1996 | Das |
| 5,591,224 A | 1/1997 | Schwartz et al. |
| 5,607,463 A | 3/1997 | Schwartz et al. |
| 5,624,411 A | 4/1997 | Tuch |
| 5,679,400 A | 10/1997 | Tuch |
| 5,722,984 A | 3/1998 | Fischell et al. |
| 5,776,184 A | 7/1998 | Tuch |
| 5,824,048 A | 10/1998 | Tuch |
| 5,824,059 A * | 10/1998 | Wijay .................. 623/1.15 |
| 5,830,879 A | 11/1998 | Isner |
| 5,837,008 A | 11/1998 | Berg et al. |
| 5,837,313 A | 11/1998 | Ding et al. |
| 5,843,158 A | 12/1998 | Lenker et al. |
| 5,865,814 A | 2/1999 | Tuch |
| 5,968,091 A | 10/1999 | Pinchuk et al. |
| 5,980,551 A | 11/1999 | Summers et al. |
| 6,017,577 A * | 1/2000 | Hostettler et al. .......... 427/2.12 |
| 6,040,408 A | 3/2000 | Koole |
| 6,077,413 A | 6/2000 | Hafeli et al. |
| 6,086,547 A | 7/2000 | Hanssen et al. |
| 6,086,773 A | 7/2000 | Dufresne et al. |
| 6,100,474 A | 8/2000 | McGregor et al. |
| 6,106,454 A | 8/2000 | Berg et al. |
| 6,110,204 A | 8/2000 | Lazarov et al. |
| 6,110,483 A * | 8/2000 | Whitbourne et al. ........ 424/423 |
| 6,113,621 A | 9/2000 | Wiktor |
| 6,176,849 B1 | 1/2001 | Yang et al. |
| 6,262,107 B1 | 7/2001 | Li et al. |
| 6,265,016 B1 | 7/2001 | Hostettler et al. |
| 6,299,604 B1 | 10/2001 | Ragheb et al. |
| 6,306,176 B1 | 10/2001 | Whitbourne |
| 6,358,556 B1 | 3/2002 | Ding et al. |
| 6,537,459 B1 | 3/2003 | Dufresne et al. |

FOREIGN PATENT DOCUMENTS

| | | |
|---|---|---|
| EP | 0895761 | 2/1999 |
| EP | 0945148 A1 | 9/1999 |
| EP | 1104681 A1 | 6/2001 |
| WO | WO 96/25897 | 8/1996 |

* cited by examiner

*Primary Examiner*—Suzette J Gherbi

(57) ABSTRACT

Radially expandable stents having hydrogel coating layers thereon, and methods of preparing such stents are disclosed. The methods include coating a wire with a solution that includes a solvent and a water soluble polymer in the solvent, evaporating the solvent to provide a polymeric coating on the wire, and crosslinking the polymeric coating to provide a hydrogel coating layer on the wire. The coated wire can be fabricated into stents, which preferably have substantially uniform coatings with low surface roughness. Preferably the coatings have hydrophilic properties and provide a biocompatible surface. The coatings may also provide for the delivery of biologically active agents into the body.

12 Claims, No Drawings

STENTS AND METHODS FOR PREPARING STENTS FROM WIRES HAVING HYDROGEL COATING LAYERS THEREON

RELATED APPLICATIONS

This application is a divisional of and claims the benefit of U.S. patent application Ser. No. 09/721,881 filed Nov. 27, 2000.

FIELD OF THE INVENTION

The present invention relates to radially expandable stents for use in humans or animals.

BACKGROUND

Radially expandable stents are widely used medical devices. A stent typically is a cylindrically shaped device formed from wire(s) or a tube and intended to act as a permanent prosthesis. A typical stent ranges from about 5 millimeters to about 50 millimeters in length. A stent is deployed in a body lumen from a radially compressed configuration into a radially expanded configuration that allows it to contact and support a body lumen. Optionally, a balloon of appropriate size and pressure can be used to open a lesion prior to delivery of the stent to its intended location.

It is known in the art of fabricating medical devices to coat stents with coating materials chosen to impart a variety of desirable properties to the device. For example, coatings have been applied to stents to improve mechanical properties and to provide for drug release and for biocompatibility. Since fabrication of a radially expandable stent from wire requires the wire to be mechanically bent a multitude of times, it is generally preferred to apply the coating to the prefabricated stent to avoid the resultant coating breaks and adhesion failures that frequently result from bending a precoated wire. As a result, the costs for applying coatings to prefabricated stents, along with the resulting coating quality, are largely controlled and limited by the fact that a batch process is being used to coat irregularly shaped objects.

A few reports of the fabrication of stents from wires that have been precoated with specific polymeric layers have appeared in the art, some examples of which may be found in the issued U.S. Patents listed in Table 1 below.

TABLE 1

Prior Art Patents

| Patent No. | Inventor(s) | Issue Date |
|---|---|---|
| 6,113,621 | Wiktor | 5 Sep. 2000 |
| 6,106,454 | Berg et al. | 22 Aug. 2000 |
| 6,100,474 | McGregor et al. | 8 Aug. 2000 |
| 6,077,413 | Hafeli et al. | 20 Jun. 2000 |
| 5,980,551 | Summers et al. | 9 Nov. 1999 |
| 5,968,091 | Pinchuk et al. | 19 Oct. 1999 |
| 5,865,814 | Tuch | 2 Feb. 1999 |
| 5,843,158 | Lenker et al. | 1 Dec. 1998 |
| 5,837,313 | Ding et al. | 17 Nov. 1998 |
| 5,837,008 | Berg et al. | 17 Nov. 1998 |
| 5,824,048 | Tuch | 20 Oct. 1998 |
| 5,776,184 | Tuch | 7 Jul. 1998 |
| 5,722,984 | Fischell et al. | 3 Mar. 1998 |
| 5,679,400 | Tuch | 21 Oct. 1997 |
| 5,624,411 | Tuch | 29 Apr. 1997 |
| 5,607,463 | Schwartz et al. | 4 Mar. 1997 |
| 5,591,224 | Schwartz et al. | 7 Jan. 1997 |
| 5,554,181 | Das | 10 Sep. 1996 |
| 5,545,211 | An et al. | 13 Aug. 1996 |
| 5,527,354 | Fontaine et al. | 18 Jun. 1996 |
| 5,525,356 | Jevne et al. | 11 Jun. 1996 |
| 5,464,650 | Berg et al. | 7 Nov. 1995 |
| 5,449,372 | Schmaltz et al. | 12 Sep. 1995 |
| 5,356,433 | Rowland et al. | 18 Oct. 1994 |
| 5,336,518 | Narayanan et al. | 9 Aug. 1994 |
| 5,330,500 | Song | 19 Jul. 1994 |
| 5,163,958 | Pinchuk | 17 Nov. 1992 |
| 5,059,166 | Fischell et al. | 22 Oct. 1991 |
| 4,886,062 | Wiktor | 12 Dec. 1989 |
| 4,795,458 | Regan | 3 Jan. 1989 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the teachings of the present invention.

U.S. Pat. No. 6,113,621 (Wiktor) discloses the fabrication of stents from polyester-coated copper wire. U.S. Pat. No. 5,968,091 (Pinchuk et al.) discloses the fabrication of stents from extrusion coated fluorinated ethylene propylene (FEP) polymer on tantalum wire. However, stents that have been fabricated from wires that have been precoated with polymeric hydrogel coatings are unknown in the art.

SUMMARY OF THE INVENTION

The present invention has certain objects. That is, various embodiments of the present invention provide solutions to one or more problems existing in the prior art respecting radially expandable stents for use in animals or humans. Those problems include inadequate mechanical properties, lack of coating uniformity, surface roughness, undesirable drug release properties, and inadequate biocompatibility. Various embodiments of the present invention have the object of solving at least one of the foregoing problems. While some radially expandable stents were capable of solving at least some of the foregoing problems, they were generally not employed because of their prohibitively high cost or difficult manufacturing processes. It is therefore another object of the present invention to provide an improved radially expandable stent that may be manufactured and sold at low cost, yet still fulfill at least one of the foregoing objects.

In comparison to known radially expandable stents, various embodiments of the present invention may provide one or more of the following advantages. The present invention provides radially expandable stents with improved properties over stents known in the art. For example, stents of the present invention are preferably provided with a substantially uniform hydrogel coating layer thereon. Coating uniformity may be important in preventing complications such as clotting that occurs during use when uncoated wire surfaces of the stent are exposed to blood.

The present invention also provides advantageous methods for producing such stents. Methods of the present invention allow the wire to be coated by a continuous process. Such continuous coating processes may provide economic advantages as well as product quality improvements. For example, continuous coating methods of the present invention preferably provide substantially uniform coatings with low surface roughness. Low surface roughness may be desirable for handling and inserting the stent into the body, and may also contribute to the reduction of blood clotting that is observed when the surface of a stent is exposed to bodily fluids such as blood.

DETAILED DESCRIPTION OF THE PREFERRED EMBODIMENTS

As used herein, "substantially uniform coating" means that the wire surface is completely covered by the coating. Preferably the stent has a coating with a uniform dry thickness of at least about 0.1 micrometer and more preferably at least about 5 micrometers. Preferably the stent has a coating with a uniform dry thickness of at most about 25 micrometers and more preferably at most about 10 micrometers. Preferably the stent has a dry coating thickness with a relative standard deviation of no greater than about 10 percent.

As used herein, "surface roughness" refers to root mean square roughness (RMS or $R_q$).

As used herein, "low surface roughness" means that sharp edges are substantially absent when the surface is observed using light microscopy at a 50 power magnification.

As used herein, "functional surface" means that the polymer used for the coating has at least the specified functional groups. The polymers can also include other functional groups. The polymers having such functional groups (amide groups, amine groups, etc.) are referred to herein as "functionalized" polymers.

A "hydrogel" is a 3-dimensional network of cross-linked, hydrophilic macromolecules capable of being swelled and incorporating about 20 percent to about 95 percent water by weight. Hydrogels may include hydrophilic polymers that absorb water, thereby changing mechanical properties. Examples of natural hydrogels include fibrin, collagen, elastin, and the like.

As used herein, "body lumen" means the inner open space or cavity of a tubular organ of the body, for example, a blood vessel or an intestine.

A "biocompatible" material is one that does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction (rejection), inflammatory reaction, or blood clotting, for example.

As used herein, "biologically active agent" means a substance that has an effect on living tissue. Biologically active agents include, for example, therapeutic agents, which are substances that tend to prevent and/or overcome disease and/or promote recovery. As such, biologically active agents also include, for example, biologically active molecules (biomolecules) such as drugs.

As used herein, "modifying cellular response" means increasing, decreasing, causing, or eliminating a response by cells to a disease, an injury, or a foreign body.

In one aspect, the present invention provides a radially expandable stent that includes a wire having a hydrogel coating layer thereon. Preferably the coating layer is substantially uniform. More preferably the stent has a hydrogel coating layer with an average dry coating thickness (T) of about 0.1 micrometer to about 25 micrometers, a standard deviation ($\sigma$), and a relative standard deviation ($100 \times \sigma/T$) of no greater than about 10 percent. The hydrogel coating layer may optionally include a biologically active agent. The coating layer preferably provides a hydrophilic, biocompatible surface.

In another aspect, the present invention provides a method for preparing a radially expandable intravascular stent, and stents that are preparable and, preferably, prepared by such a method. The method includes providing a metal wire; applying to the wire a solution that includes a solvent and a water soluble polymer in the solvent; evaporating the solvent to provide a polymeric coating on the wire; crosslinking the polymeric coating to provide a hydrogel coating layer on the wire; and fabricating the coated wire into a cylindrical, radially expandable stent body. Preferably the solution is applied to the wire by a continuous coating method such as, for example, passing the wire through the solution at a substantially constant speed. The hydrogel coating layer may optionally be swollen with water prior to fabricating the coated wire into a stent.

In another aspect, the present invention provides a method for delivery of a biologically active agent to the interior of a body lumen. In one embodiment, the method includes providing a metal wire; applying to the wire a solution that includes a solvent, a water soluble polymer in the solvent, and a biologically active agent dispersed in the solvent; evaporating the solvent to provide a polymeric coating on the wire; crosslinking the polymeric coating to provide a hydrogel coating layer on the wire; fabricating the coated wire into a cylindrical, radially expandable stent body; introducing the stent body transluminally into a selected portion of the body lumen; and radially expanding the stent body into contact with the body lumen. In another embodiment, the method includes providing a metal wire; applying to the wire a solution that includes a solvent and a water soluble polymer in the solvent; evaporating the solvent to provide a polymeric coating on the wire; crosslinking the polymeric coating to provide a hydrogel coating layer on the wire; fabricating the coated wire into a cylindrical, radially expandable stent body; applying a biologically active agent to the hydrogel coating layer; introducing the stent body transluminally into a selected portion of the body lumen; and radially expanding the stent body into contact with the body lumen.

In another aspect, the present invention provides a method of modifying cellular response in a body lumen to a disease, injury, or foreign body. In one embodiment, the method includes providing a metal wire; applying to the wire a solution that includes a solvent, a water soluble polymer in the solvent, and a biologically active agent dispersed in the solvent; evaporating the solvent to provide a polymeric coating on the wire; crosslinking the polymeric coating to provide a hydrogel coating layer on the wire; fabricating the coated wire into a cylindrical, radially expandable stent body; introducing the stent body transluminally into a selected portion of the body lumen; radially expanding the stent body into contact with the body lumen; and controllably releasing the biologically active agent into the body lumen. In another embodiment, the method includes providing a metal wire; applying to the wire a solution that includes a solvent and a water soluble polymer in the solvent; evaporating the solvent to provide a polymeric coating on the wire; crosslinking the polymeric coating to provide a hydrogel coating layer on the wire; fabricating the coated wire into a cylindrical, radially expandable stent body; applying a biologically active agent to the hydrogel coating layer; introducing the stent body transluminally into a selected portion of the body lumen; radially expanding the stent body into contact with the body lumen; and controllably releasing the biologically active agent into the body lumen.

The present invention provides novel radially expandable stents and methods for fabricating such stents. A water soluble polymer is coated onto a wire, the solvent is evaporated, and the polymer is crosslinked to provide a hydrogel coating layer on the wire. The coated wire is then fabricated into a stent. Preferably the water soluble polymer is coated onto the wire using a continuous coating process. Continuous solution coating processes are capable of providing substantially uniform coatings, resulting in stents with improved coating uniformity compared to coated stents known in the art.

Wire useful for articles and methods of the present invention includes drawn low-memory level material such as stainless steel, titanium ASTM F63-83 Grade 1, and high carat gold K 19-22. Copper alloy (e.g., 110) when properly coated with polyester or poly(tetrafluoroethylene) can also be used. Titanium and gold are biocompatible, inert, and require no special treatment. Preferably the wire is stainless steel or tantalum. The diameter of the wire is preferably about 50 micrometers to about 200 micrometers.

Optionally the wire may be pretreated or precoated with, for example, gold, ceramics, polymers, and vapor deposited materials. For example, a wire may be precoated with a polysulfone to promote adhesion of a hydrogel coating layer. A polysulfone precoating layer may be applied, for example, by any suitable solvent coating and drying method. If a polymer is used as the pretreatment layer, the resulting dry coating thickness is preferably about 0.01 micrometer to about 1 micrometer.

A "hydrogel" is 3-dimensional network of cross-linked, hydrophilic macromolecules capable of being swelled and incorporating about 20 percent to about 95 percent water by weight. Hydrogel coating may be prepared by coating a solution of a water soluble polymer, and then crosslinking the polymeric coating. The crosslinking reaction may occur during a drying step or as a separate step.

Hydrogel coating solutions useful for articles and methods of the present invention include a water soluble polymer dissolved, dispersed, or suspended in a solvent to provide a coating solution. Optionally, the coating solution may contain other functional and/or non-functional additives including, but not limited to, initiators, crosslinking agents, biologically active agents, and polymers with functional groups. Preferably the coating solution includes at least about 1 percent by weight polymer and more preferably at least about 10 percent by weight polymer. Preferably the coating solution includes at most about 90 percent by weight polymer and more preferably at most about 25 percent by weight polymer.

Hydrogel coatings useful for articles and methods of the present invention may be selected by using appropriate screening tests. Such exemplary tests include a coil test. In such a test, a coated wire is coiled around a stainless steel wire of 2 mm thickness that is being rotated at 100 revolutions per minute. The resulting coil of coated wire is then visually analyzed using light microscopy at a 50 power magnification. The coated wire may be tested as either in the dried state or in the swollen state that results from immersion in a fluid, preferably an aqueous fluid such as, for example, saline or water. Coatings tested in the swollen state that show no visible cracks using this coiling method are considered mechanically stable and suitable as wire coatings for stents and methods of the present invention. Preferably the coatings show no visible cracks when tested in the dry state using this coiling method.

Polymers that may be used to prepare hydrogel coatings useful for articles and methods of the present invention preferably have substantial flexibility. Flexibility may arise from the use of a polymer with a low $T_g$, for example, a polymer with a $T_g$ of less than about 25° C. Alternatively, a polymer with a higher $T_g$ may be swollen or plasticized to achieve adequate flexibility. In the case of hydrogels, the presence of water may lead to the desired flexibility.

Polymers that may be used to prepare solvent based coatings useful for articles and methods of the present invention preferably are not only flexible, but also have substantial toughness. Flexibility and toughness may arise, for example, from the use of polymers that contain both hard and soft segments, with the hard segments being, for example, crystalline segments (e.g., having both amorphous and crystalline segments).

Crosslinking the polymers during or after the coating process may also develop adequate toughness. Preferably the solvent coating solution includes low $T_g$ (e.g., a $T_g$ of less than about 25° C.) crosslinkable polymers (e.g., hydrogels). The level of crosslinking may be controlled to provide the desired physical properties (e.g., toughness, rate of drug release, etc.).

Polymers useful in the present invention include polymers that are soluble, dispersable, or suspendable in the particular solvent being used. Organic polymers having hydrocarbon backbones are preferred. Useful polymers include, but are not limited to, poly(hydroxyethyl methacrylate) (pHEMA), poly (vinylpyrrolidinone) (PVP), poly(acrylamide) (pAM), and poly(acrylic acid) (pAA). Preferably the polymer is chosen so as to adhere to the wire and to provide a hydrophilic surface after coating and drying. More preferably the polymer provides a biocompatible surface or a functional surface that can be modified to provide a biocompatible surface.

Solvents useful in coating solutions for articles and methods of the present invention include solvents that can be removed from the coated wire at drying temperatures of about 50° C. to about 200° C. Useful solvents generally have a boiling point of about 40° C. to about 200° C. Solvents useful in coating solutions of the present invention include, for example, tetrahydrofuran, acetone, ethanol, isopropanol, water, methylene chloride, chloroform, hexane, heptane, xylenes, and toluene.

Crosslinking agents may optionally be added to the coating solution to modify the physical and chemical properties of the dried coating as desired. Suitable crosslinking agents include, but are not limited to, functional, multifunctional, and polyfunctional materials, including, for example, acrylate, acrylamide, or epoxide functionalities. When crosslinking agents are used, they are typically added in about 0.1 percent by weight to about 50 percent by weight based on the weight of the polymer.

When crosslinking agents are used in the solvent coating, initiators may be added to facilitate crosslinking. For example, when polyacrylate crosslinking agents are used, a free-radical generating initiator may be included. Suitable free-radical generating initiators may be activated by light or heat. Preferred initiators include, for example, ammonium persulfate. When initiators are used, they are typically added in about 0.0001 percent by weight to about 0.01 percent by weight based on the weight of the monomer.

Coating methods known in the art may be used to apply the coating solution to the wire for articles and methods of the present invention. Preferably the method is a continuous coating method. A particularly useful method for applying coatings for articles and methods of the present invention is to pass a wire at a substantially constant speed through the coating solution. For example, the wire may be pulled in a vertical direction from the solution to provide a substantially uniform coating. Optionally, the wire may be passed through a die to remove excess coating. When using continuous coating methods, useful coating speeds will depend on factors such as the percent solids of the coating solution, viscosity of the coating solution, and temperature of the coating solution. Preferably the wire may be coated at about 1 lineal meters per minute to about 100 lineal meters per minute. The temperature of the coating solution may be maintained at any temperature desired, for example, at 25° C.

After the coating is applied, it may be dried by methods known in the art. Suitable drying methods include, but are not limited to, conduction drying, convection drying, hot air impingement, steam treatment, infrared irradiation, ultraviolet irradiation, and microwave irradiation. Preferably the coating is dried by the application of heat. Preferably the coated wire is dried with air at a temperature of about 50° C. to about 200° C. for about 0.01 second to about 100 seconds.

Preferably the coating is applied so as to result in a dry coating thickness of at least about 0.1 micrometer and preferably at least about 5 micrometers. Preferably the coating is applied so as to result in a dry coating thickness of at most about 25 micrometers and more preferably at most about 10 micrometers.

Preferably the coating and drying methods are selected so as to provide a substantially uniform coating. Adequate uniformity may be determined by visually inspecting the coated wire to ensure that no uncoated wire is exposed. Alternatively, surface uniformity of the coating may be measured by field emission spectrometry (FEM), with a substantially uniform coating showing complete coverage of the wire.

Preferably the coating and drying methods are selected so as to provide a coating with a substantially uniform thickness as measured by the standard deviation ($\sigma$). Preferably for a coating of dry thickness T, the relative standard deviation ($100 \times \sigma/T$) is no greater than about 10 percent.

Preferably the coating and drying methods are selected so as to provide a coating with low surface roughness. Surface roughness may be measured using, for example, laser profilometry. Preferably the relative surface roughness ($100 \times R_q/T$) is at most about 25 percent and more preferably at most about 10 percent. Alternatively, the surface roughness may be qualitatively evaluated by microscopic examination. Generally, the uncoated wire surface visually appears to have a rougher surface than the coated surface when coated by the method of the present invention. Preferably the coating has low surface roughness as evidenced by sharp edges being substantially absent. Moreover, wire used for articles and methods of the present invention need not be polished in order to obtain stents with good surface roughness properties.

For some applications it is preferable that the coating be swellable when immersed in fluids, preferably aqueous fluids such as, for example, saline or water. For coatings containing biologically active agents, for example, swelling of the coating in bodily fluids will enhance the release of the biologically active agents. The rate and degree of swelling may be chosen to provide the desired release properties.

The solvent coated wire can be fabricated into a radially expandable stent by methods known in the art. For example, U.S. Pat. No. 4,886,062 (Wiktor) discloses a vascular stent and a method for preparing the stent. Initially a wire is preformed by folding into a two-dimensional zig-zag pattern, typically a sinusoidal pattern. A length of the patterned wire under little or no tension is then wound around a mandrel, and the mandrel removed to provide a radially expandable stent. The fabrication may be carried out with dried or wet coatings. If desired, the fabrication can be carried out by folding the wire while the wire is immersed in a solution. For example, when using hydrogel coatings, it is useful to fabricate the stent with the wire immersed in water to maintain the hydrogel coating in the wet or swollen state. Alternatively, the solvent coated wire may also be fabricated into stents using other techniques known in the art.

Biologically active agents may be added to coated radially expandable stents of the present invention by adding the biologically active agent to the coating solution or by applying the biologically active agent to the coated hydrogel layer. If the biologically active agent is applied to the coated hydrogel layer, the application may take place either before or after the coated wire has been fabricated into a stent as desired. The biologically active agent may be applied to the hydrogel coating in either the dry or the wet state. Application of the biologically active agent to the hydrogel coating in the wet or swollen state is preferred for incorporating the biologically active agent more uniformly throughout the coating. Suitable application methods include, for example, dip coating. Biologically active agents may be added to stents to provide, for example, biocompatible surfaces. Useful biologically active agents include, but are not limited to, dipyridamole, heparin, anti-platelet drugs, anti-thrombogenic drugs, anti-proliferative drugs, and anti-mitotic drugs. When biologically active agents are used, they are typically added in about 0.1 percent by weight to about 25 percent by weight based on the weight of the polymer.

Coatings used in the stents and methods of the present invention may be selected and formulated to controllably release biologically active agents at the desired rate. The rate of release may depend on, for example, the amount and type of biologically active agent present in the coating and the temperature and conditions of the desired release. The rate of release may also depend on the properties of the selected polymer including, for example, solubility and polarity. Other factors may also effect the rate of release including, for example, crosslink density.

The surface coated radially expandable stents of the present invention may also be used for immobilizing biologically active agents. For example, when polyacrylamide is used as the wire coating, an amide-functional surface is obtained. The amide functional surface may be converted to an amine-functional surface by the Hoffman degradation process as described in copending U.S. patent application Ser. No. 09/245,834 filed 8 Feb. 1999 entitled "METHOD FOR ATTACHMENT OF BIOMOLECULES TO SURFACES THROUGH AMINE-FUNCTIONAL GROUPS." Biologically active agents (e.g., periodate-activated heparin, collagen) may be readily coupled to the amine-functional surface. See, for example, U.S. Pat. Nos. 5,607,475 and 5,679,659.

Biologically active agents may be attached in an appropriate amount and orientation effective to provide, for example, an improved nonthrombogenic surface relative to the substrate without the biologically active agent. The present invention provides relatively high biologically active agent loading capacities (often as high as 50 micrograms of biologically active agents per square centimeter of modified surface) and bioactivities (often as high as 1.0 International Unit (IU) thrombin (IIa) deactivated per square centimeter of modified surface).

The present invention is illustrated by the following examples. It is to be understood that the particular examples, materials, amounts, and procedures are to be interpreted broadly in accordance with the scope and spirit of the invention as set forth herein.

EXAMPLES

Hydroxyethyl methacrylate (HEMA, 99.9 percent purity) was obtained from Kodak (Rochester, N.Y.). Electrophoresis grade acrylamide (99.9 percent purity was obtained from Aldrich Chemicals Inc. (Milwaukee, Wis.). Polyvinylpyrrolidone (povidone, PVP, Average $M_w$ ca. 1,300,000 daltons was obtained from Aldrich Chemicals Inc. (Milwaukee, Wis.).

Ammonium persulfate was obtained from from Aldrich Chemicals Inc. (Milwaukee, Wis.). Deionized water was used for all reactions.

Example 1

A solution of poly(hydroxyethyl methacrylate) is prepared by free radical polymerization of hydroxyethyl methacrylate (20 percent by weight) in water using ammonium persulfate initiator (up to 0.01 percent by weight) at 50° C. Prior to use as a coating solution, a bis-acrylate is added up to a concentration of about 0.01 percent by weight.

Example 2

A solution of polyacrylamide is prepared by free radical polymerization of acrylamide (20 percent by weight) in water using ammonium persulfate initiator (up to 0.01 percent by weight) at 50° C. Prior to use as a coating solution, a bis-acrylamide is added up to a concentration of about 0.01 percent by weight.

Example 3

A solution of poly(vinyl pyrrolidone) is prepared by dissolving PVP (20 percent by weight) in water. Prior to use as a coating solution, vinyl pyrrolidone is added up to a concentration of about 5 percent by weight and an initiator is added up to a concentration of about 0.01 percent by weight.

Example 4

The solutions prepared in Examples 1-3 are used to coat stainless steel wire (125 micrometers thick, Fort Wayne, Ind.) and tantalum wire (125 micrometers thick, Fort Wayne, Ind.) in a continuous process. Each wire is pulled through a solution of the desired polymer at a rate of 1 to 2 meters/second into an infrared dying oven of approximately 1 meter in length at about 100° C. The wires are completely covered indicating the application of a substantially uniform coating.

The flexibility of the coated wires are tested using the following method. A dry coated wire is coiled around a stainless steel wire of 2 mm thickness that is being rotated at 100 revolutions per minute. The resulting coil of coated wire is then visually analyzed using light microscopy at a 50 power magnification. The coatings showing no visible cracks using this coiling method are considered mechanically stable and suitable as wire coatings for stents and methods of the present invention.

Example 5

A solution of poly(vinyl pyrrolidone) was prepared by dissolving PVP (20 percent by weight) in water. Prior to use as a coating solution, vinyl pyrrolidone was added up to a concentration of about 5 percent by weight, and an initiator was added up to a concentration of about 0.01 percent by weight. Unfractionated heparin (Diosynth, Oss, N L) was added to the solution at a concentration of up to 5 percent by weight. Stainless steel wires and tantalum wires were coated and dried as described in Example 4 to give a dry coating thickness of 5 micrometers.

Pieces of wire were incubated with a solution of phosphate buffered saline at 37° C. Samples were taken over time and assayed for heparin activity via determination of the rate of inactivation of a thrombin-antithrombin III mixture. It was concluded that approximately 15 percent of the heparin that was incorporated in the coating was released within 2 hours. Additional incubation of the coating resulted in a much slower release (10 percent in two days).

Example 6

A solution of poly(vinyl pyrrolidone) was prepared by dissolving PVP (20 percent by weight) in water. Prior to use as a coating solution, vinyl pyrrolidone was added up to a concentration of about 5 percent by weight, and an initiator was added up to a concentration of about 0.01 percent by weight. Dipyridamole (Merck, Darmstadt, GDR) was added to the solution at a concentration of up to 20 percent by weight. Stainless steel wires and tantalum wires were coated and dried as described in Example 4 to give a dry coating thickness of 5 micrometers.

Pieces of wire were incubated with phosphate buffered saline (pH=7.4) at 37° C. The solution was assayed periodically using ultraviolet-visible spectrometry. During the first 90 minutes approximately 20 percent of the drug was released. This burst was followed by release at a much slower rate. Additional incubation of the wire during a period of two days gave an additional release of 10 percent.

Example 7

Stainless steel wires and tantalum wires were coated with PVP and dried as described in Example 4 to give a dry coating thickness of approximately 4 micrometers. Pieces of coated wire were incubated with a $Na_2CO_3$ buffer (pH=10) at 60° C. for one hour to induce hydrolysis of some of the vinyl pyrrolidone rings. After thorough rinsing, the pieces were soaked in a solution of 0.5 percent by weight poly(allylamine) (Mw=1500, Aldrich), in a 0.25M 4-morpholineethane-sulfonic acid solution (pH=5.5) containing 0.05M 1-ethyl-3-(3-dimethylaminopropyl)carbodiimide hydrochloride. The reaction was allowed to proceed for one hour at room temperature after which the samples were rinsed with deionized water.

A solution of unfractionated heparin (5 mg/ml) in 0.05M phosphate buffer (pH=6.88) was prepared. $NalO_4$ (0.065 mg/ml, Aldrich) was added to the solution to induce periodate oxidation for introduction of aldehyde groups into the heparin chains. The reaction was allowed to proceed for 3 hours at room temperature.

The resulting solution was diluted 1:5 by volume with 0.4M acetate buffer (pH=4.66). $NaBH_3CN$ (0.4 mg/ml, Aldrich) was added and the aminated samples were incubated with the resulting periodate oxidized heparin solution for 18 hours at room temperature. The samples were then rinsed with deionized water, 1 M NaCl, and deionized water again. Staining of the samples with Toluidine blue revealed an abundance of immobilized heparin.

Incubation of the heparinized samples with a solution of antithrombin III resulted in adsorbed activated antithrombin III that was capable of deactivation of thrombin when contacted with a solution containing the latter. This showed that the immobilized heparin was bioactive.

The complete disclosure of all patents, patent applications, and publications, and electronically available material cited herein are incorporated by reference.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to methacrylate, acrylamide, or poly(vinyl pyrrolidone) based hydrogel coated stents. The present invention is also not limited to hydrogel coated stents per se, but may find further applications such as, for example, biocompatible medical devices. The present invention further includes within its scope methods of making and using the stents described hereinabove.

What is claimed is:

1. A radially expandable stent comprising a wire having a hydrogel coating layer thereon, wherein the stent is preparable by a method comprising:
   providing a metal wire;
   applying to the wire a solution that includes a solvent and a water soluble polymer in the solvent;
   evaporating the solvent to provide a polymeric coating on the wire;
   crosslinking the polymeric coating to provide a hydrogel coating layer on the wire; and
   fabricating the coated wire into a cylindrical, radially expandable stent body, wherein the hydrogel coating layer is swollen with an aqueous fluid prior to fabricating the coated wire into a stent.

2. The stent of claim 1 wherein the solution is applied to the wire by a continuous coating method.

3. The stent of claim 2 wherein the continuous coating method comprises passing the wire through the solution at a substantially constant speed.

4. A method for making a radially expandable intravascular stent comprising:
   providing a metal wire;
   applying to the wire a solution that includes a solvent and a water soluble polymer in the solvent;
   evaporating the solvent to provide a polymeric coating on the wire;
   crosslinking the polymeric coating to provide a hydrogel coating layer on the wire; and
   fabricating the coated wire into a cylindrical, radially expandable stent body, wherein the hydrogel coating layer is swollen with an aqueous fluid prior to fabricating the coated wire into a stent.

5. The method of claim 4 wherein the solution is applied to the wire by a continuous coating method.

6. The method of claim 5 wherein the continuous coating method comprises passing the wire through the solution at a substantially constant speed.

7. The method of claim 4 wherein the hydrogel coating layer has an average dry coating thickness of about 0.01 micrometer to about 25 micrometers.

8. The method of claim 4 wherein the thickness of the hydrogel coating layer has a relative standard deviation of no greater than about 10 percent.

9. A method for delivery of a biologically active agent to the interior of a body lumen comprising:
   providing a metal wire;
   applying to the wire a solution that includes a solvent, a water soluble polymer in the solvent, and a biologically active agent dispersed in the solvent;
   evaporating the solvent to provide a polymeric coating on the wire;
   crosslinking the polymeric coating to provide a hydrogel coating layer on the wire;
   fabricating the coated wire into a cylindrical, radially expandable stent body, wherein the hydrogel coating layer is swollen with an aqueous fluid prior to fabricating the coated wire into a stent;
   introducing the stent body transluminally into a selected portion of the body lumen; and
   radially expanding the stent body into contact with the body lumen.

10. A method for delivery of a biologically active agent to the interior of a body lumen comprising:
    providing a metal wire;
    applying to the wire a solution that includes a solvent and a water soluble polymer in the solvent;
    evaporating the solvent to provide a polymeric coating on the wire;
    crosslinking the polymeric coating to provide a hydrogel coating layer on the wire;
    fabricating the coated wire into a cylindrical, radially expandable stent body, wherein the hydrogel coating layer is swollen with an aqueous fluid prior to fabricating the coated wire into a stent;
    applying a biologically active agent to the hydrogel coating layer;
    introducing the stent body transluminally into a selected portion of the body lumen; and
    radially expanding the stent body into contact with the body lumen.

11. A method of modifying cellular response in a body lumen to a disease, injury, or foreign body, comprising:
    providing a metal wire;
    applying to the wire a solution that includes a solvent, a water soluble polymer in the solvent, and a biologically active agent dispersed in the solvent;
    evaporating the solvent to provide a polymeric coating on the wire;
    crosslinking the polymeric coating to provide a hydrogel coating layer on the wire;
    fabricating the coated wire into a cylindrical, radially expandable stent body, wherein the hydrogel coating layer is swollen with an aqueous fluid prior to fabricating the coated wire into a stent;
    introducing the stent body transluminally into a selected portion of the body lumen;
    radially expanding the stent body into contact with the body lumen; and
    controllably releasing the biologically active agent into the body lumen.

12. A method of modifying cellular response in a body lumen to a disease, injury, or foreign body, comprising:
    providing a metal wire;
    applying to the wire a solution that includes a solvent and a water soluble polymer in the solvent;
    evaporating the solvent to provide a polymeric coating on the wire;
    crosslinking the polymeric coating to provide a hydrogel coating layer on the wire;
    fabricating the coated wire into a cylindrical, radially expandable stent body, wherein the hydrogel coating layer is swollen with an aqueous fluid prior to fabricating the coated wire into a stent;
    applying a biologically active agent to the hydrogel coating layer;
    introducing the stent body transluminally into a selected portion of the body lumen;
    radially expanding the stent body into contact with the body lumen; and
    controllably releasing the biologically active agent into the body lumen.

* * * * *